(12) United States Patent
Sekiguchi

(10) Patent No.: US 8,948,491 B2
(45) Date of Patent: Feb. 3, 2015

(54) METHOD AND APPARATUS FOR DETECTING SURFACE UNEVENNESS OF OBJECT UNDER INSPECTION

(75) Inventor: Toshikatsu Sekiguchi, Tokyo (JP)

(73) Assignee: Kabushiki Kaisha Bridgestone, Tokyo (JP)

( * ) Notice: Subject to any disclaimer, the term of this patent is extended or adjusted under 35 U.S.C. 154(b) by 636 days.

(21) Appl. No.: 13/060,551

(22) PCT Filed: Aug. 25, 2009

(86) PCT No.: PCT/JP2009/064795
§ 371 (c)(1),
(2), (4) Date: Feb. 24, 2011

(87) PCT Pub. No.: WO2010/024254
PCT Pub. Date: Mar. 4, 2010

(65) Prior Publication Data
US 2011/0188731 A1 Aug. 4, 2011

(30) Foreign Application Priority Data
Aug. 26, 2008 (JP) ................................ 2008-217117

(51) Int. Cl.
*G06K 9/00* (2006.01)
*G01B 11/30* (2006.01)
(Continued)

(52) U.S. Cl.
CPC ................ *G01B 11/30* (2013.01); *G01N 21/95* (2013.01); *G01N 21/952* (2013.01)
USPC ........... 382/141; 382/154; 382/164; 382/165; 356/600; 356/606

(58) Field of Classification Search
USPC ........... 382/141, 154, 164, 165; 356/600, 606
See application file for complete search history.

(56) References Cited

U.S. PATENT DOCUMENTS 5,987,978 A * 11/1999 Whitehead ...................... 73/146
6,124,925 A 9/2000 Kaneko et al.
(Continued)

FOREIGN PATENT DOCUMENTS

JP 58-092904 A 6/1983
JP 61-198009 A 9/1986
(Continued)

OTHER PUBLICATIONS

International Search Report for International Application No. PCT/JP2009/064795 dated Oct. 6, 2009.

*Primary Examiner* — Kim Vu
*Assistant Examiner* — Michael Vanchy, Jr.
(74) *Attorney, Agent, or Firm* — Sughrue Mion, PLLC

(57) ABSTRACT

Minute surface unevenness formed on the surface of an object under inspection is detected, thereby improving the accuracy of an appearance inspection. A target surface in the sidewall region (21) of a tire (20) is illuminated by a red slit light from a first illuminating means (11) disposed in the direction of 45 degrees with respect to the normal line to the target surface. At the same time, the target surface is illuminated by a blue slit light from a second illuminating means (12) disposed in the direction of −45 degrees with respect to the normal line. The illuminated surface is shot by a line camera (13) from the direction of the normal line. An R-component image and a B-component image are produced from the original image, and their respective luminance distribution waveforms are obtained. The surface unevenness formed on the target surface is detected on the basis of the luminance distribution waveforms.

7 Claims, 8 Drawing Sheets

(51) Int. Cl.
    *G01N 21/95*    (2006.01)
    *G01N 21/952*    (2006.01)

(56) References Cited

U.S. PATENT DOCUMENTS

| | | | |
|---|---|---|---|
| 6,327,374 B1 * | 12/2001 | Piironen et al. | 382/108 |
| 6,600,567 B2 * | 7/2003 | Kaneko et al. | 356/601 |
| 6,757,065 B1 | 6/2004 | Hansson et al. | |
| 7,092,105 B2 * | 8/2006 | Lim et al. | 356/601 |
| 2001/0045125 A1 | 11/2001 | Alexander | |
| 2005/0058333 A1 * | 3/2005 | Kaneko et al. | 382/141 |

FOREIGN PATENT DOCUMENTS

| | | |
|---|---|---|
| JP | 08-21709 A | 1/1996 |
| JP | 10-89939 A | 4/1998 |
| JP | 11-138654 A | 5/1999 |
| JP | 2002-228417 A | 8/2002 |
| JP | 2002-535668 A | 10/2002 |
| JP | 2003-139714 A | 5/2003 |
| JP | 2003-202214 A | 7/2003 |
| JP | 2003-240521 A | 8/2003 |
| JP | 2005-148010 A | 6/2005 |

* cited by examiner

METHOD AND APPARATUS FOR DETECTING SURFACE UNEVENNESS OF OBJECT UNDER INSPECTION

CROSS REFERENCE TO RELATED APPLICATIONS

This application is a National Stage of International Application No. PCT/JP2009/064795 filed Aug. 25, 2009, which claims priority from Japanese Patent Application No. 2008-217117 filed Aug. 26, 2008, the contents of all of which are incorporated herein by reference in their entirety.

TECHNICAL FIELD

The present invention relates to a method for detecting surface unevenness of an object under inspection, such as a tire or tire part, and an apparatus therefore.

BACKGROUND ART

As conventional methods for detecting surface unevenness (asperity) of an object under inspection by image processing, there are the light-section method for measuring surface shape and the image-based determination method using a color camera (refer to Patent Documents 1 to 3, for example).

The light-section method goes as follows: For example, as a tire is rotated, a slit light is cast at a surface of the tire by an illuminating means capable of casting monochromatic light such as a semiconductor laser, and the portion illuminated by the slit light is shot by an area camera. Then after the two-dimensional coordinates of the shot slit image are obtained, the outer shape of the tire is derived by converting the two-dimensional coordinates into three-dimensional coordinates using the angle of rotation of the tire. Thus, by comparing this outer shape against reference images stored in advance, tire shapes in the bead region, the tread region, the sidewall region, and the like can be inspected.

On the other hand, in the proposed image-based determination method using a color camera, a white slit light is cast at the surface of an object under inspection, and the reflected image is shot by a line camera. And from the shot color image, surface unevenness (indentations and bumps), state of undulation, or subtle changes in color of the surface of the object under inspection are detected. Note, however, that it is not necessary that the line camera be a color camera. And a grayscale image of the object under inspection may be shot using a monochromatic light as the slit light, and surface unevenness, state of undulation, or subtle changes in color may be detected from the shades of the shot image.

PRIOR ART DOCUMENT

Patent Document

Patent Document 1: Japanese Unexamined Patent Application Publication No. 11-138654
Patent Document 2: Japanese Unexamined Patent Application Publication No. 2003-240521
Patent Document 3: Japanese Unexamined Patent Application Publication No. 2003-139714

SUMMARY OF THE INVENTION

Problems to be Solved by the Invention

In the case of the light-section method, however, it has been difficult to distinguish very small unevenness (minute asperity) of 0.5 mm or less in depth, such as "bares" that can occur on tire surface in the curing process, from optical noise due to the moiré effect since the depth of the indentations is shallow.

Also, in the determination of surface unevenness using color images, it has been difficult to distinguish the minute asperity from optical noise such as color unevenness or shading on the tire surface.

The present invention has been made in view of such problems of the known arts, and an object thereof is to improve the accuracy of appearance inspection of an object under inspection by detecting relatively shallow indentations on the surface thereof also.

Means for Solving the Problem

As shown in FIG. 8, slit light is cast at the surface of an object under inspection 1 at different angles from an illuminating means 2, and the images thereof are shot by a camera 3 from the direction vertical to the object under inspection 1. When the slit light is cast from the right side of an indentation 4, the intensity of reflected light entering the camera 3 from the indentation 4 is higher if the direction of planar vector is closer to the direction ($\alpha 1$) of the slit light as in the case of indentation surface $4a$ (x=x1) and lower if the direction of planar vector is farther away from the direction ($\alpha 1$) of the slit light as in the case of indentation surface $4b$ (x=x2).

Through close and diligent investigations, the inventor has conceived the present invention based on the following realization. If slit lights are cast from a plurality of mutually different directions (the simplest case being two directions ($\alpha 1$, $\alpha 2$) as shown in FIG. 8 and the indentation 4 is shot with a camera, there will be a shift between the peak positions of luminance distribution waveforms of the reflected images from the plurality of slit lights. Therefore, by comparing the luminance levels in a region containing the peak positions of the plurality of reflected images having the shift in the peak position, it is possible to determine whether there is an indentation 4 in the surface of the object under inspection 1. Furthermore, if a plurality of slit lights of mutually different wavelengths are cast simultaneously from a plurality of mutually different directions and a reflected image from the illuminated portion is shot with a camera, and then if a plurality of reflected images are produced by separating the reflected image into the reflected images for the respective wavelengths through image processing, then it is possible to obtain, by a single shooting, the luminance distribution waveforms of the reflected images from the plurality of slit lights.

Thus, according to a first aspect of the present invention, there is provided a method for detecting surface unevenness of an object under inspection, which comprises the steps of casting slit lights from a plurality of directions at a same portion on a target surface of the object under inspection while moving the object under inspection relative to illuminating means and image pickup means, shooting reflected images of the portion illuminated by the slit lights respectively with the image pickup means, obtaining luminance distribution waveforms for the plurality of reflected images respectively, and detecting surface unevenness of the object under inspection based on the obtained plurality of luminance distribution waveforms.

According to a second aspect of the present invention, there is provided a method for detecting surface unevenness of an object under inspection, which comprises the steps of casting slit lights of mutually different wavelengths at a target surface of the object under inspection simultaneously from a plurality of directions while moving the object under inspection relative to illuminating means and image pickup means, shooting a reflected image of the portion illuminated by the slit lights with the image pickup means, separating the reflected image into reflected images for the respective wavelengths by image processing of the reflected image, obtaining luminance distribution waveforms for the separated reflected images respectively, and detecting surface unevenness of the object under inspection based on the respective luminance distribution waveforms.

According to a third aspect of the present invention, there is provided an apparatus for detecting surface unevenness of an object under inspection, which comprises illuminating means for casting slit light at a target surface of the object under inspection, image pickup means for shooting a portion illuminated by the slit light, moving means for moving the illuminating means and image pickup means and the object under inspection relative to each other, and surface unevenness detecting means for detecting surface unevenness of the object under inspection based on luminance of a slit image shot by the image pickup means, in which the illuminating means has a plurality of illuminating units for casting a plurality of illuminating lights of different wavelengths at a target surface of the object under inspection from mutually different directions, in which the image pickup means shoots a reflected image of the slit lights from the plurality of illuminating units, and in which the surface unevenness detecting means obtains luminance distribution waveforms for the respective wavelengths by image processing of the reflected image to separate it into reflected images for the respective wavelengths and detects surface unevenness of the object under inspection based on the luminance distribution waveforms obtained for the respective wavelengths.

According to a fourth aspect of the present invention, there is provided an apparatus for detecting surface unevenness of an object under inspection, in which the surface unevenness detecting means further comprises calculating means for calculating a degree of uneven surface inclination in the target surface of the object under inspection, using the incident directions of the plurality of illuminating lights to the target surface of the object under inspection, the ratio of intensity of the plurality of illuminating lights of different wavelengths, and the ratio of luminance of reflected images for the respective wavelengths, and detecting means for detecting surface unevenness of the target surface by comparing the calculated degree of inclination against a preset threshold value. Note that in calculating the ratio of intensity of the illuminating lights, it is advisable that one of the plurality of illuminating units is used as the reference illuminating unit and the intensity of illuminating light of other illuminating units is calculated relative to the intensity of illuminating light of the reference illuminating unit. Also, in calculating the ratio of luminance of the plurality of reflected images for the respective wavelengths, it is preferable that the luminance of the reflected image of the illuminating light of the reference illuminating unit is used as the reference.

According to a fifth aspect of the present invention, there is provided an apparatus for detecting surface unevenness of an object under inspection, in which the illuminating unit has a first illuminating unit and a second illuminating unit, and in which the image pickup means is installed between the first illuminating unit and the second illuminating unit in a same plane as the first and second illuminating units so as to shoot the reflected image of slit lights from the first and second illuminating units.

According to a sixth aspect of the present invention, there is provided an apparatus for detecting surface unevenness of an object under inspection as recited in claim 5, in which the image pickup means is installed in a direction vertical to the target surface of the object under inspection, and in which the first and second illuminating units are disposed in a plane defined by the image pickup means and a direction of motion of the object under inspection and also in positions symmetrical to each other with respect to the shooting direction of the image pickup means.

According to a seventh aspect of the present invention, there is provided an apparatus for detecting surface unevenness of an object under inspection, in which the illuminating directions of the first and second illuminating units are within a range of 30 to 60 degrees to the target surface, respectively.

According to an eighth aspect of the present invention, there is provided an apparatus for detecting surface unevenness of an object under inspection, in which the slit light from one of the first and second illuminating units is a blue light (for example, laser beam whose central wavelength is about 450 nm) and the slit light from the other thereof is a red light (for example, laser beam whose central wavelength is about 680 nm).

Effect of the Invention

According to the present invention, in detecting surface unevenness of an object under inspection from the luminance of reflected image shot with slit light cast at a target surface S thereof, the luminance distributions of a plurality of reflected images are obtained by shooting the reflected images with the slit light cast from a plurality of mutually different directions. At the same time, the surface unevenness of the object under inspection is detected, for instance, based on the luminance level of reflected light when the light is cast atone face of inclination of an indentation in the surface of the object under inspection from a direction closer to the verticality to the face and the luminance level of reflected light from the opposite face. In this manner, the surface unevenness of the object under inspection is detected from the reflected images shot when the indentations and bumps on the object under inspection are illuminated from different directions. Therefore, it is possible to detect minute surface unevenness, such as "bares" in the sidewall of the tire also.

In such an arrangement, the reflected images may be shot with slit lights of mutually different wavelengths cast simultaneously from a plurality of mutually different directions, and the luminance distributions of the reflected images for the respective wavelengths may be derived. Then it is possible to obtain reflected images from a plurality of directions, which can be separated from each other, by a single measurement. Therefore, the detection of surface unevenness is made easier, and besides the detection accuracy can be improved because there is no need for position adjustment for the plurality of images.

Also, the degree of uneven surface inclination of a target surface of the object under inspection may be calculated using the plurality of incident directions of illuminating light to the target surface of the object under inspection, the ratio of intensity of the plurality of illuminating lights of different wavelengths, and the ratio of luminance of the plurality of reflected images of different wavelengths, and the surface unevenness of the target surface may be detected by comparing the calculated degree of uneven surface inclination against a preset threshold value. Then the detection accuracy of surface unevenness can be further improved because the optical noise can be removed completely.

Also, when the illuminating unit is to be two units, namely, a first illuminating unit and a second illuminating unit, the image pickup means may be installed between the first illuminating unit and the second illuminating unit in the same plane as the first and second illuminating units, and the image pickup means may shoot the reflected images of slit lights from the first and second illuminating units. Then the detection accuracy of surface unevenness can be further improved because the reflected images of illumination by slit lights from front and back or from right and left can be obtained.

Also, the image pickup means may be installed in the direction vertical to the target surface of the object under inspection, and the first and second illuminating units are disposed in positions symmetrical to each other with respect to the shooting direction of the image pickup means. Then the shift in the peak position of the luminance distributions can be detected with excellent accuracy because the shooting conditions for the two images may be substantially the same.

Also, to avoid obstruction of the illuminating light by projections, such as tire markings, and to prevent the range of reflected lights from being too narrow, it is preferable that the illuminating directions of the first and second illuminating units are within a range of 30 to 60 degrees to the target surface.

Also, when the reflected images are to be separated from each other for each wavelength, the separation is easier if the wavelength of the slit light from the first illuminating unit and the wavelength of the slit light from the second illuminating unit are wide apart from each other. Therefore, the difference in the peak position of the luminance distributions can be detected with good accuracy if one slit light is a red light and the other is a blue light.

BEST MODE FOR CARRYING OUT THE INVENTION

Preferred embodiments of the present invention will be described hereinbelow with reference to the accompanying drawings. This does not intend to limit the scope of the present invention, but to exemplify the invention.

Figure 1:
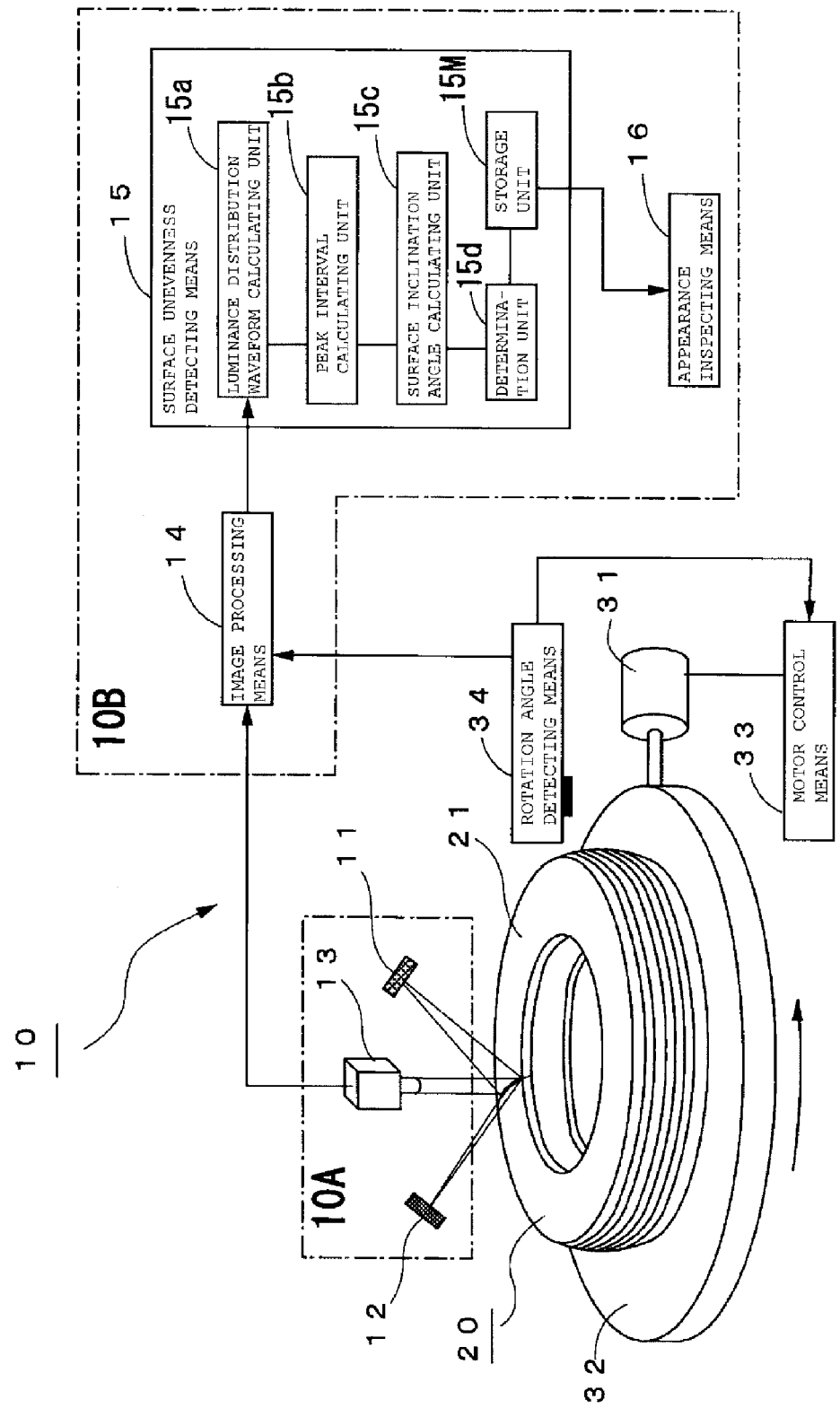
FIG. 1 is a schematic diagram of a tire appearance inspection apparatus according to a preferred embodiment of the present invention.

FIG. 1 is a diagram showing a schema of a tire appearance inspection apparatus 10 according to a preferred embodiment of the present invention. In the figure, reference numeral 11 and 12 denote a first and a second illuminating means for casting slit light at a sidewall region 21 of a tire 20 mounted on a rotary table 32 that is rotated by a motor 31, 13 a line camera for shooting an image of the portion illuminated by the slit light (illuminated portion), 14 an image processing means for processing the image shot by the line camera 13, 15a surface unevenness detecting means for detecting minute surface unevenness of the sidewall region 21, and 16 an appearance inspecting means for inspecting the appearance of the tire 20 based on the numbers and sizes of the indentations and bumps (surface unevenness) detected. The first and second illuminating means 11 and 12 and the line camera 13 constitute an image pickup unit 10A of the tire appearance inspection apparatus 10, whereas the image processing means 14, the surface unevenness detecting means 15, and the appearance inspecting means 16 constitute a computation unit 10B thereof.

The tire 20, which is the object under inspection, is mounted on the rotary table 32 in such a manner that the sidewall region 21 faces up, which means that the axial direction of the tire is in agreement with the direction of rotation axis of the rotary table 32. The rotary table 32 rotates at a predetermined rotational speed set by the drive/control signals from the motor control means 33 which drives and controls the motor 31. Also, the angle of rotation of the tire 20 is detected by the rotation angle detecting means 34 placed near the rotary table 32.

Figure 2A:
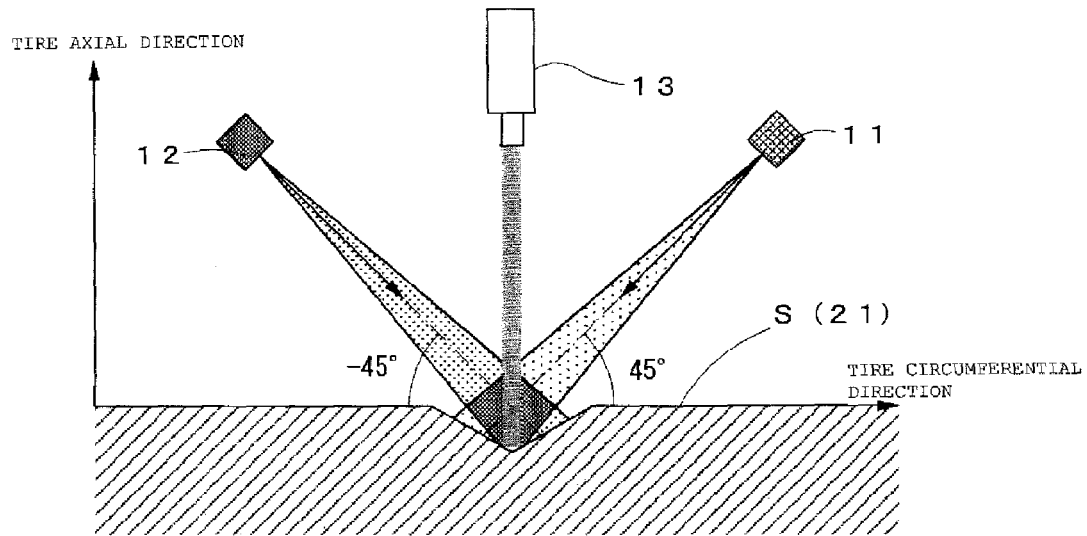
FIG. 2 is illustrations showing an arrangement of an image pickup unit.
Figure 2B:
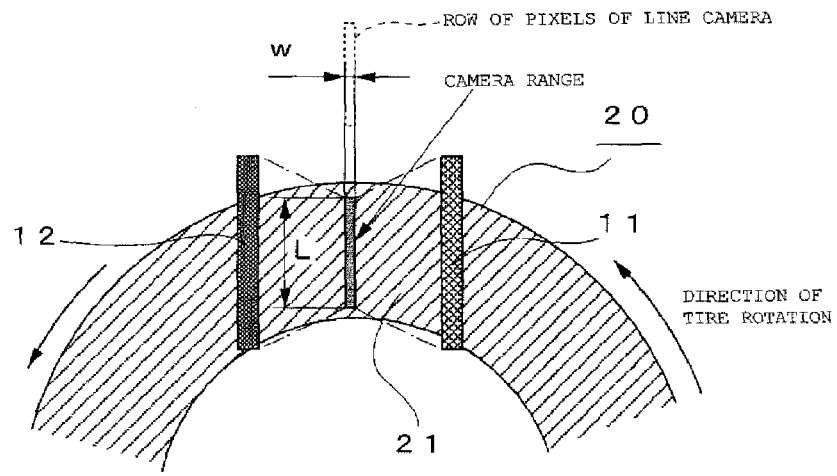

The line camera 13, which is a CCD color camera with its pixels arranged in a row, is installed above the center of the sidewall region 21 of the tire 20 (above in the tire axial direction) in such an orientation that the direction of the row of pixels is orthogonal to the tire circumferential direction. The surface of the sidewall region 21 opposite to the line camera 13 is a target surface S of the tire 20 under inspection. Also, the first and second illuminating means 11 and 12 are each a semiconductor laser arranged on a line, with the semiconductor laser of the first illuminating means 11 directing a laser beam (red light) whose central wavelength being about 680 nm at the target surface S and the semiconductor laser of the second illuminating means 12 directing a laser beam (blue light) whose central wavelength being about 450 nm at the target surface S. The first illuminating means 11 is disposed in a position above the target surface S and on the front side as viewed in the direction of tire rotation (on the side with smaller tire rotation angle) such that the illuminating direction of slit light is 45 degrees with respect to the target surface S. The second illuminating means 12 is disposed in a position above the target surface S and on the rear side as viewed in the direction of tire rotation (on the side with larger tire rotation angle) such that the illuminating direction of slit light is −45 degrees with respect to the target surface S. Note that the sign of the angle as used herein is "+" counterclockwise up to the vertical to the target surface S, as shown in FIG. 2(a).

In other words, the line camera 13 is installed in the axial direction of the tire 20, which is the direction vertical to the target surface S of the object under inspection. And the first and second illuminating means 11 and 12 are disposed in a plane defined by the line camera 13 and the direction of rotation of the tire 20 (tire circumferential direction) as well as in positions symmetrical to each other with respect to the shooting direction of the line camera 13.

The image processing means 14 produces two kinds of images, namely, an R-component image and a B-component image, by separating an image shot by the line camera 13 (hereinafter referred to as an original image) into an R component and a B component.

The surface unevenness detecting means 15 includes a luminance distribution waveform calculating unit 15a, which calculates the respective luminance distribution waveforms along the tire circumferential direction using the luminance data from the pixels of the two kinds of images, a peak interval calculating unit 15b, which calculates the shift length between the peak position of the luminance distribution waveform of the R-component image and that of the B-component image, a surface inclination angle calculating unit 15c, which calculates the surface inclination angle θ indicating the degree of uneven surface inclination of the target surface S when the shift length is a predetermined value or greater, a determination unit 15d, which detects surface unevenness by comparing the calculated surface inclination angle θ against a preset threshold value to determine whether the spot with a shift between the two peak positions is attributable to a surface unevenness, and a storage unit 15M, which stores the center position of the detected surface unevenness and the surface inclination angle θ. Thus, the surface unevenness detecting means 15 detects minute surface unevenness of 0.5 mm or less in depth in the images by comparing the two kinds of images and stores the data. Note that the surface inclination angle θ is calculated using the inclination of the target surface of the object under inspection, the incident direction of illuminating light from the first illuminating means, the incident direction of illuminating light from the second illuminating means, the ratio of intensity of the illuminating lights of different wavelengths, and the ratio of luminance of the reflected images for the different wavelengths.

The appearance inspecting means 16 inspects the acceptability of the appearance of the tire 20 based on the number and size of the detected indentations and bimps.

Figure 3:
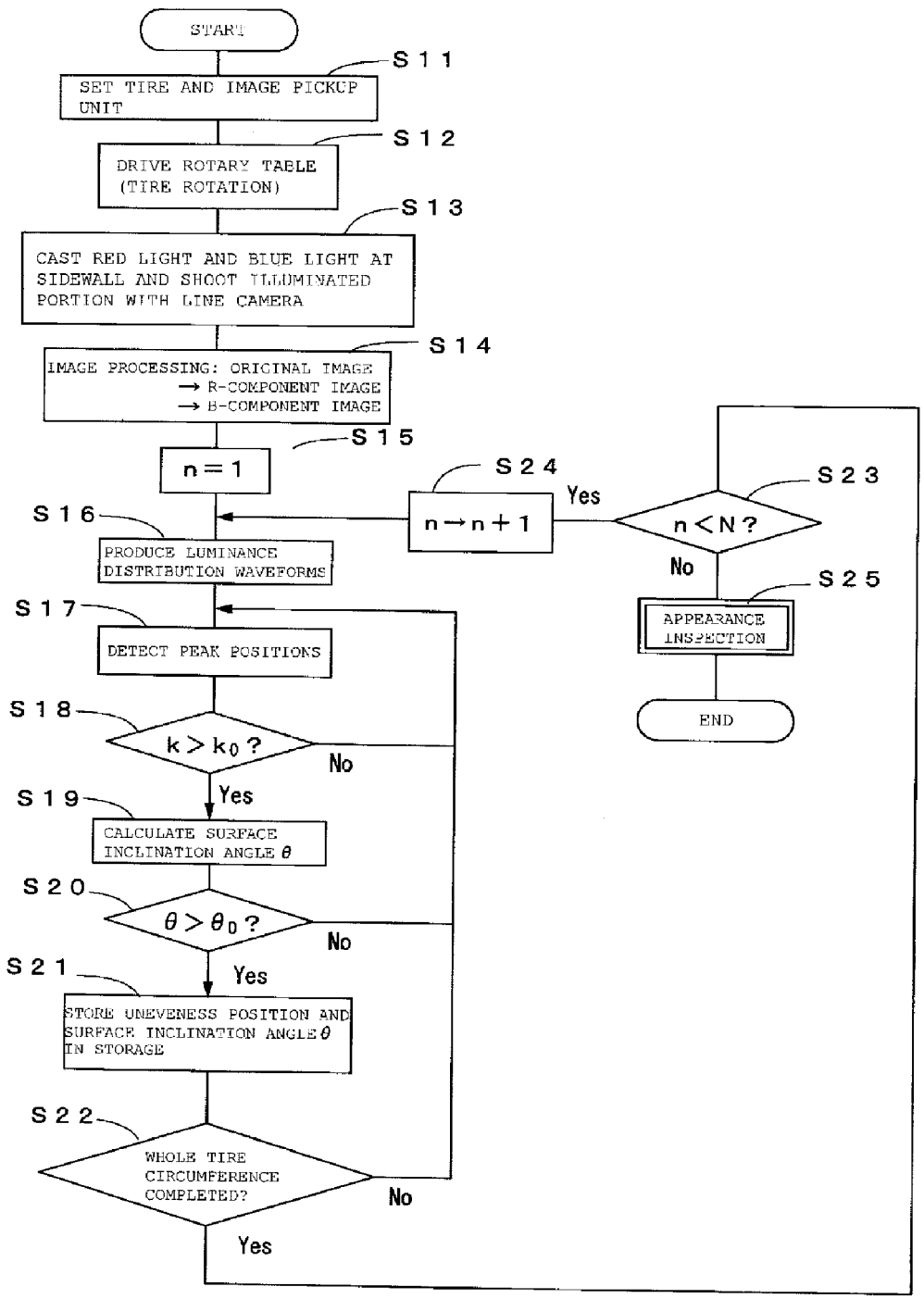
FIG. 3 is a flowchart showing a method for inspecting the appearance of a sidewall region of a tire.

Next, an appearance inspection method for the sidewall region 21 of a tire using a tire appearance inspection apparatus 10 according to the present embodiment will be explained by referring to the flowchart of FIG. 3.

First a tire 20, which is the object under inspection, is mounted on a rotary table 32, and also an image pickup unit 10A, which consists of a line camera 13 and first and second illuminating means 11 and 12, is set directly above the sidewall region 21 of the tire 20 (S11). Then the tire 20 is rotated at a predetermined rotation speed by rotating the rotary table 32 through drive/control of the motor 31 (S12).

Next, a red slit light and a blue slit light are cast at a target surface S respectively from the first and second illuminating means 11 and 12, which are installed above the sidewall region 21 of the tire, and at the same time the image of the illuminated portion, where the two slit lights are cast, is shot by the line camera 13 (S13). In the present embodiment, the shooting width W of the line camera 13 is 10 μm, the shooting range L thereof is 135 mm, and the illuminated portion is shot in 50 μm steps. Note that the coordinates of the shot portion are calculated from the rotation angle of the tire 20 as detected by the rotation angle detecting means 34 and the position and the shooting range L of the line camera 13.

Figure 4:
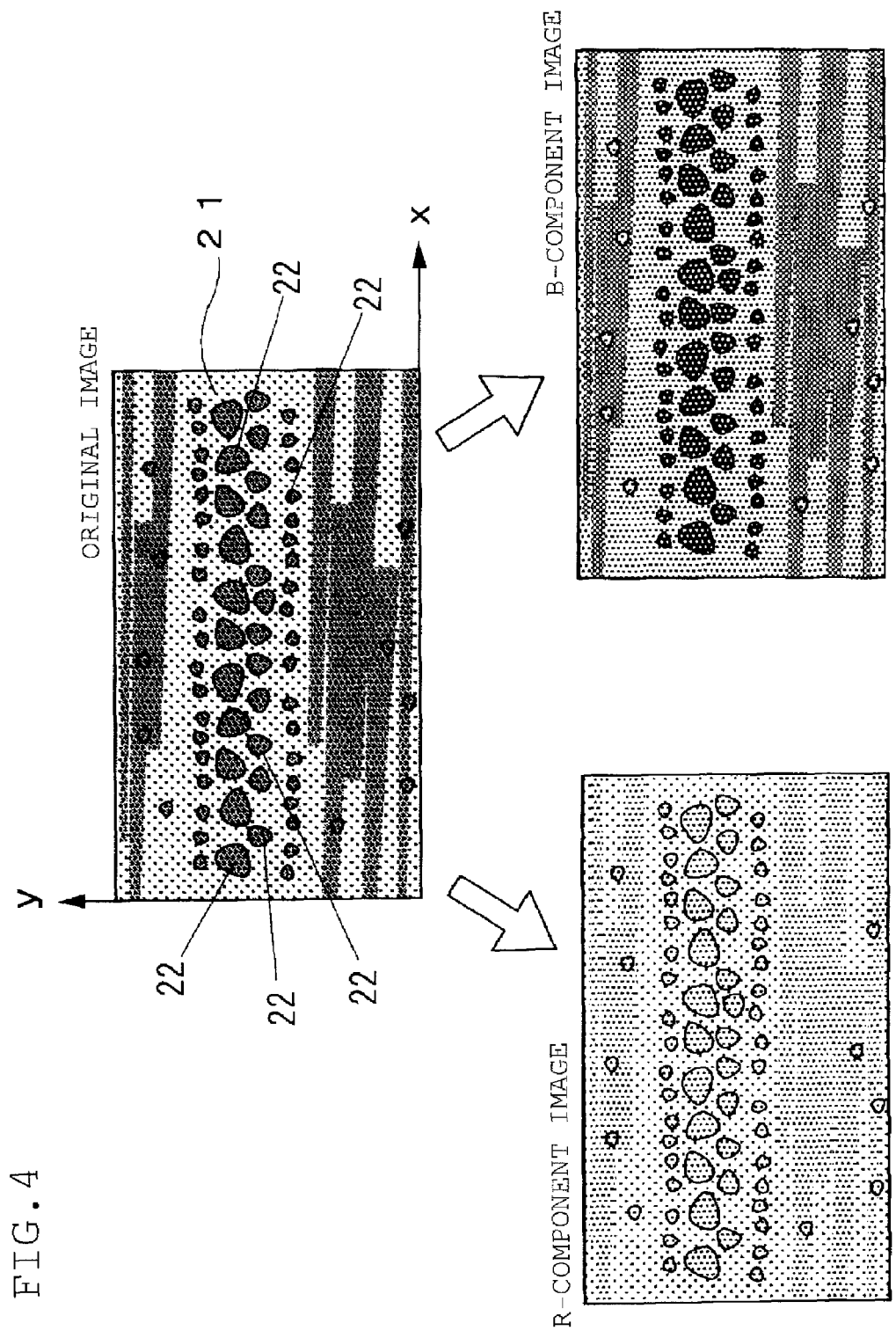
FIG. 4 is schematic depictions of an original image, a R-component image, and a B-component image of a sidewall region.

In the present embodiment, as shown in FIG. 4, an R-component image and a B-component image are produced from an original image/an image (hereinafter referred to as an original image), which is an image shot of the illuminated portion illuminated by the R slit light and the B slit light. It is to be noted, however, that FIG. 4 is not the original image itself, but is a schematic depiction of an original image of the part having shallow surface unevenness, taken from a shot image of the sidewall region 21. In the figure, the horizontal axis (x axis) represents the tire circumferential direction, and the vertical axis (y axis) the tire radial direction. The surface unevenness shown in it is the indentations called "bare" which are created by the gas remaining between the mold and the green tire in the curing process. An appearance rejection is decided on the tire if the bares 22 are deep and wide.

The original image is sent to an image processing means 14. The color data from the pixels of the original image are all obtained as a superposition (composite) of luminance data of the R component, luminance data of the G component, and luminance data of the B component. Therefore, the image processing means 14 carries out an image processing of first separating the color data of all the pixels of the original image into the luminance data of the R component and the luminance data of the B component and then producing an R-component image from the luminance data of the R component of the pixels and a B-component image from the luminance data of the B component thereof (S14).

Since the R-component image and the B-component image are both a two-dimensional image, the luminance distributions of these images become three-dimensional luminance distribution curves with the x axis being the tire circumferential direction, the y axis being the tire radial direction and the z axis being the luminance level. The luminance distribution curves are the luminance distribution waveforms along the tire circumferential direction superposed on top of one another in the tire radial direction.

Figure 5:
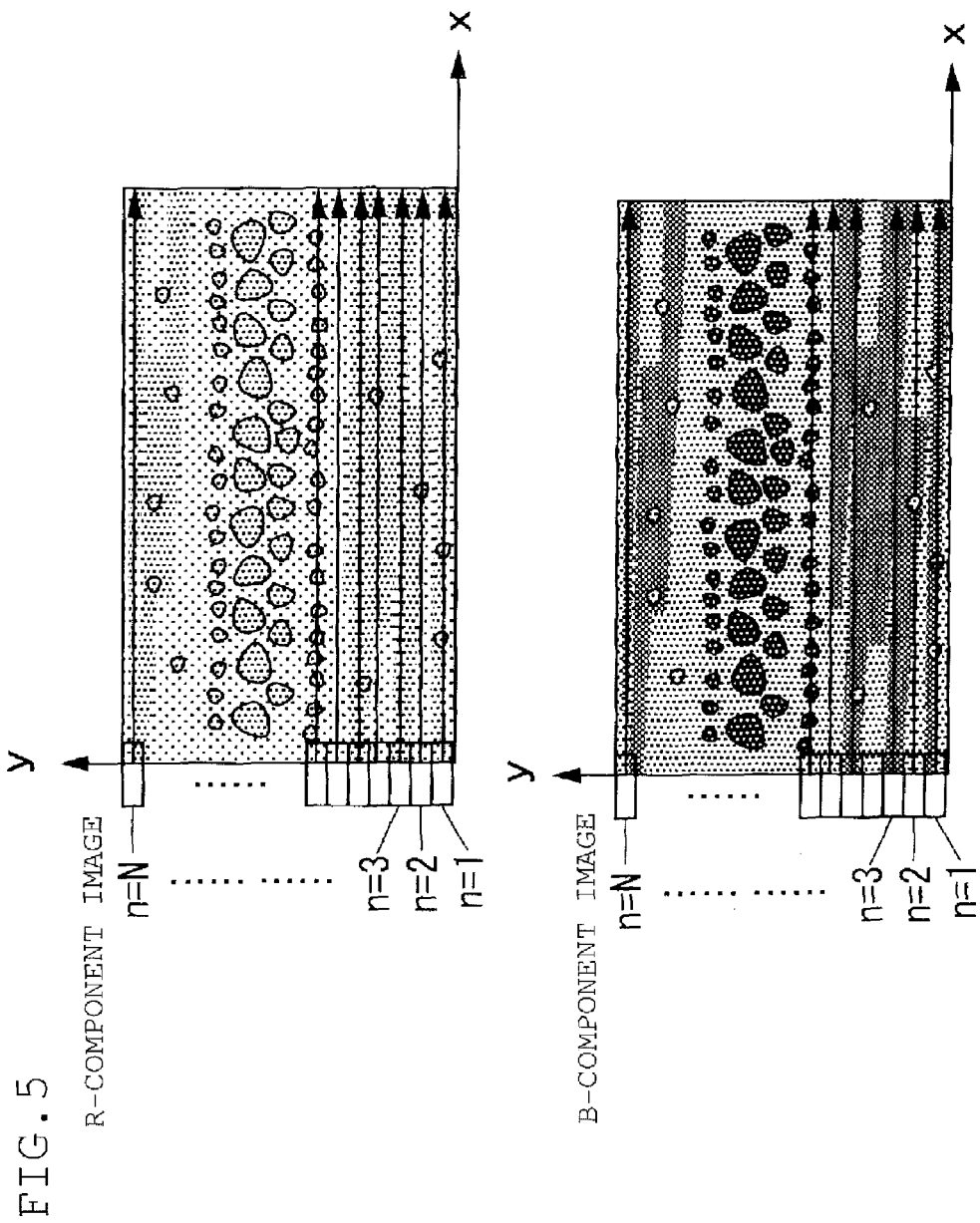
FIG. 5 is illustrations showing an example of a method of generating luminance distribution waveforms.

In the present embodiment, as shown in FIG. 5, the R-component image and the B-component image are each divided into N parts in the tire radial direction. And first the surface unevenness of the target surface S is detected using the luminance distribution waveform along the tire circumferential direction at the radially innermost position (n=1) in the target surface S in the tire radial direction (y-axis direction) of the sidewall region 21. Then the surface unevenness is detected sequentially at the positions of n=2, n=3, . . . until at the radially outermost position (n=N).

Figure 6:
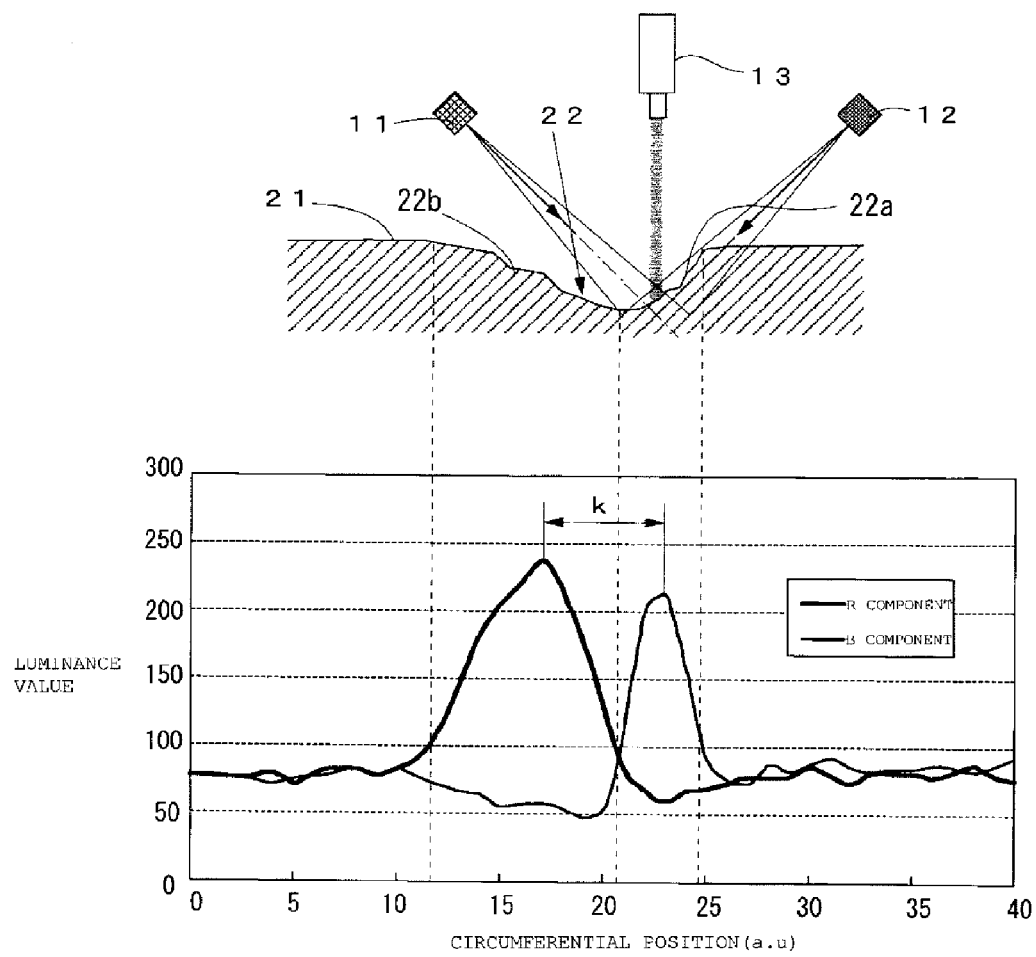
FIG. 6 is a diagram showing the luminance distribution waveforms of an R-component image and a B-component image.

First the position in the tire radial direction (y-axis direction) to obtain a luminance distribution waveform is set to n=1 (S15). Then the R-component image and the B-component image sent from the image processing means 14 are each scanned along the tire circumferential direction (x-axis direction), with the position in the y-axis direction fixed at n=1, thus obtaining the luminance data of the respective images. And a graph showing two luminance distribution waveforms, which are the luminance distribution waveform of the R-component image and the luminance distribution waveform of the B-component image along the tire circumferential direction, as shown in FIG. 6, of which the horizontal axis represents the circumferential positions of the tire 20 with the origin being the shooting start position and the vertical axis represents the luminance values (S16).

Next, the peak positions of the two luminance distribution waveforms are detected by scanning along the tire circumferential direction (x-axis direction) with the position in the y-axis direction fixed at n=1 (S17). If there exists a bare in the target surface S of the object under inspection, then the shift between the peak position of the luminance distribution waveform of the R-component image and the peak position thereof of the B-component image becomes marked. Without any surface unevenness in the target surface S, the red light from the first illuminating means 11 and the blue light from the second illuminating means 12 are both cast at the target surface S in such a manner that both the reflected light of the red light and the reflected light of the blue light enter the line camera 13 substantially the same way. However, when there is a bare 22 in the target surface 22, an inside wall 22a of the bare 22 is illuminated with the red light from the first illuminating means 11 but not with the blue light from the second illuminating means 12. Conversely, another inside wall 22b of the bare 22 is illuminated with the blue light from the second illuminating means 12 but not with the red light from the first illuminating means 11.

When the shift length k between the peak position of the luminance distribution waveform of the R-component image and the peak position thereof of the B-component image is less than a predetermined length $k_0$ (for example, $k_0$=0.15 mm), the likelihood is that it may not represent an unevenness of tire surface from the viewpoint of detection accuracy. In the present embodiment, therefore, the shift length k of the peak positions is compared against the predetermined length $k_0$ (S18). And if the shift length k is the predetermined length $k_0$ or greater, which suggests the presence of a bare 22, the procedure goes to the next step S19, where a surface unevenness is detected. If the shift length k is smaller than the predetermined length $k_0$, it is assumed that there is no surface unevenness. Then the procedure returns to the step S17, where the next peak positions are detected.

In step S19, the surface inclination angle θ is calculated, which provides a reference by which to determine whether the cause of the shift between the peak position of the luminance distribution waveform of the R-component image and that of the B-component image is clearly a bare 22 or indistinguishable among a stain, a discoloration, and a bare 22.

The surface inclination angle θ from a scanning in the tire circumferential direction is calculated as follows:

Let p denote the surface inclination in the tire circumferential direction and q the surface inclination in the tire radial direction of point P (x, y, z) on the target surface S. Then p and q can be expressed as:

$$P = \frac{\partial z}{\partial x} \quad q = \frac{\partial z}{\partial y} \qquad \text{[Equation 1]}$$

Using p and q, the normal vector $\vec{n}$ of the target surface S can be expressed as:

$$\vec{n} = \frac{1}{\sqrt{P^2 + q^2 + 1}}(-p, -q, 1) \qquad \text{[Equation 2]}$$

On the other hand, the incident light vector $\vec{S}_R$ of the red light cast by the first illuminating means 11 and the incident light vector $\vec{S}_B$ of the blue light cast by the second illuminating means 12, when the intensity of the red light is denoted by $I_R$ and that of the blue light by $I_B$, can be expressed as:

$$\vec{S}_R = \frac{I_R}{\sqrt{P_R^2 + q_R^2 + 1}}(-p_R, -q_R, 1) \qquad \text{[Equation 3]}$$

$$\vec{S}_B = \frac{I_B}{\sqrt{P_B^2 + q_B^2 + 1}}(-p_B, -q_B, 1)$$

Also, as represented by the equations below, the intensity $E_R$ of red light inputted to the line camera 13 is the orthogonal projection of the incident light vector $\vec{S}_R$ to the normal vector $\vec{n}$ multiplied by the reflectivity ρ of the tire 20, which is the object under inspection, and the intensity $E_B$ of blue light inputted to the line camera 13 is the orthogonal projection of the incident light vector $\vec{S}_B$ to the normal vector $\vec{n}$ multiplied by the reflectivity ρ thereof.

$$\vec{E}_R = \rho(\vec{S}_R \cdot \vec{n}) = \qquad \text{[Equation 4]}$$

$$\rho I_R \frac{1}{\sqrt{p^2 + q^2 + 1}} \frac{1}{\sqrt{p_R^2 + q_R^2 + 1}}(pp_R + qq_R + 1)$$

$$\vec{E}_B = \rho(\vec{S}_B \cdot \vec{n}) =$$

$$\rho I_B \frac{1}{\sqrt{p^2 + q^2 + 1}} \frac{1}{\sqrt{p_B^2 + q_B^2 + 1}}(pp_B + qq_B + 1)$$

Figure 7A:
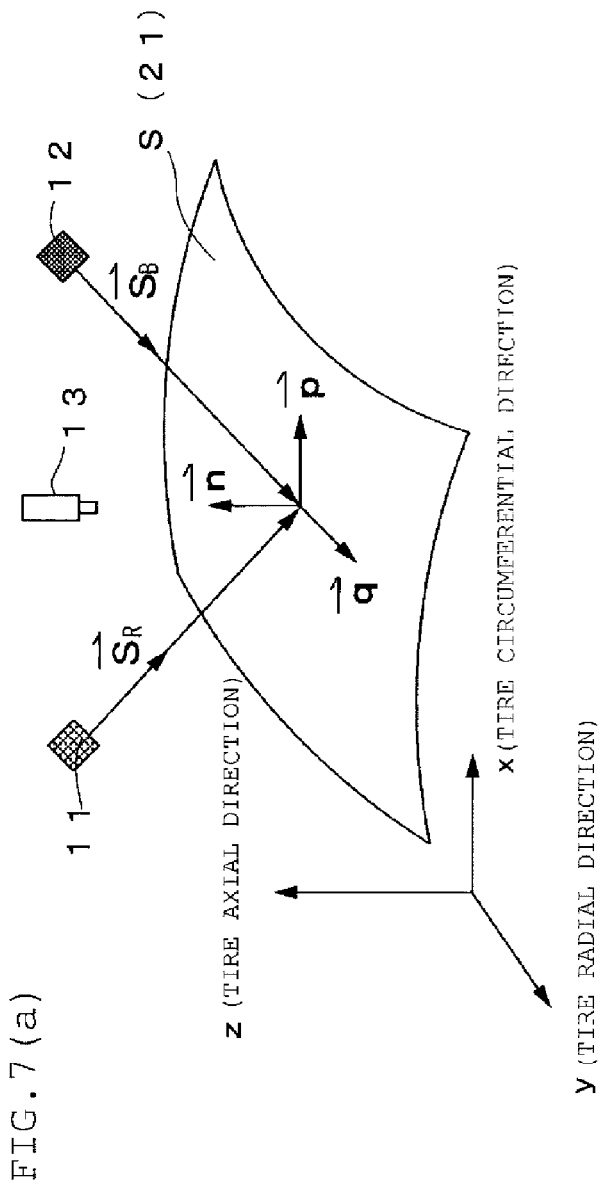
FIG. 7 is a diagram for explaining a method for calculating a surface inclination angle θ.
Figure 7B:
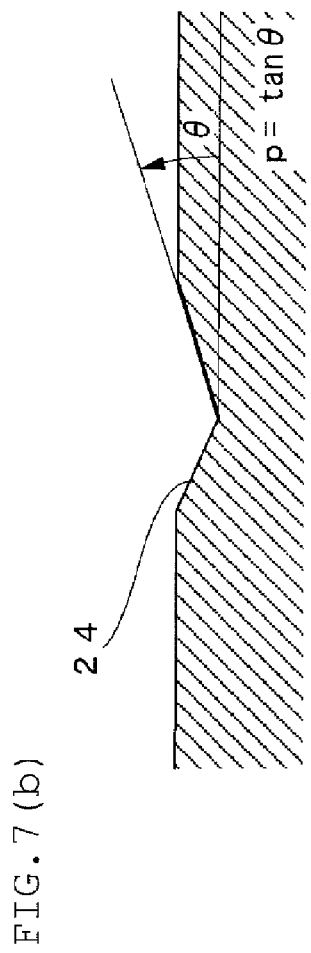
Figure 8:
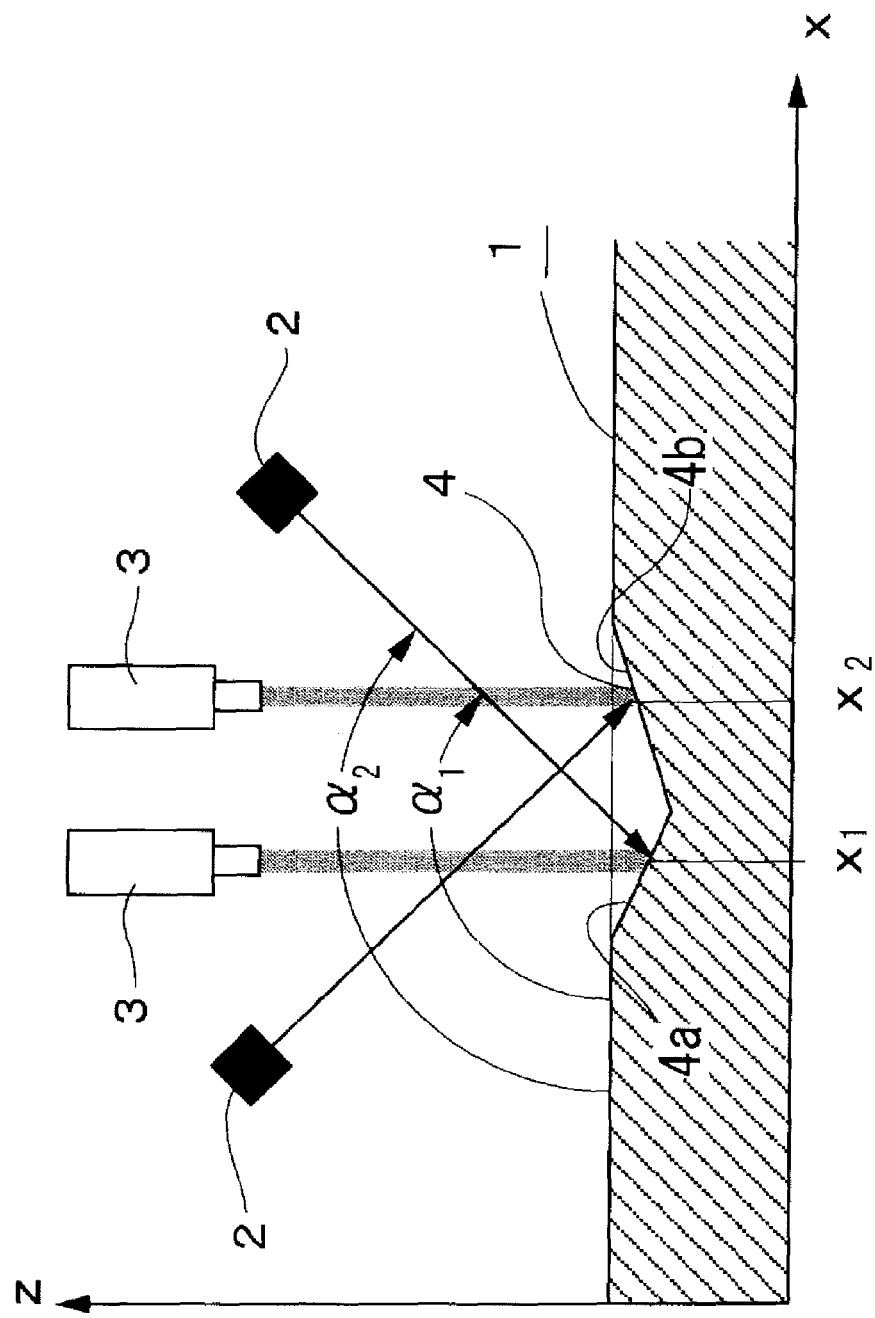
FIG. 8 is an illustration showing a measurement principle in a surface unevenness detection according to the present invention.

The inclination p in the tire circumferential direction of the target surface S can be obtained by eliminating the inclination q in the tire radial direction from the above equation of the intensity $E_R$ of red light and the above equation of the intensity $E_B$ of blue light. It is to be noted that, as shown in FIG. 7B, the above-mentioned p is in a relationship of p=tan θ with the surface inclination angle θ, which is the degree of inclination of the inside wall of the surface unevenness (indentation) 24 in an x-z cross section of the sidewall region 21. Accordingly, the surface inclination angle θ can be expressed as:

$$\theta = \tan^{-1} p = \tan^{-1} \frac{\alpha - 1}{p_R - \alpha \cdot p_B} \left( \alpha = \frac{\sqrt{p_R^2 + 1}}{\sqrt{p_B^2 + 1}} \cdot \frac{E_R}{E_B} \cdot \frac{I_B}{I_R} \right) \qquad \text{[Equation 5]}$$

The above calculation is performed by the surface inclination angle calculating unit 15c.

Next, the determination unit 15d determines whether the surface unevenness 24 having the surface inclination angle θ is a real unevenness like the bare 22 or not by comparing the calculated surface inclination angle θ against a preset threshold value (S20). More specifically, a lower limit $\theta_0$ of the surface inclination angle θ is set as the threshold value, and the calculated surface inclination angle θ is compared with the lower limit $\theta_0$. If $\theta \geq \theta_0$, then it is determined that the surface unevenness 24 exists, and the position of the surface unevenness 24 and the surface inclination angle θ are stored in the storage unit 15M (S21). In the present embodiment, the midpoint of the x coordinates of the two peak positions is used as the x coordinate (position in the tire circumferential direction) of the surface unevenness 24. Note that the y coordinate (position in the tire radial direction) is the scanning start position in the tire radial direction (position of n=1 here).

On the other hand, if $\theta < \theta_0$, then it is determined that there is no surface unevenness 24 since the surface unevenness 24 is indistinguishable among a stain, a discoloration, and a bare 22.

On completion of the above determination, the procedure goes to step S22, where a check is made if the surface unevenness detection has been completed for the whole circumference of the tire. If the surface unevenness detection has not been completed for the whole circumference of the tire, the procedure goes back to step S17, where the peak position of the luminance distribution waveform of the R-component image and the peak position thereof of the B-component image are detected and the surface unevenness detection is performed again.

Also, when the surface unevenness detection for the whole circumference of the tire has been completed, a check is made if the position in the tire radial direction is at the final position, namely, n=N (S23). At this point, however, the position n=1 is completed, and therefore n<N. Therefore, the position in the tire radial direction is advanced by 1 (S24), and then the procedure goes back to step S16, where the luminance data of the respective images are obtained by the scanning along the tire circumferential direction (x-axis direction) at the position of n=2, and the luminance distribution waveform of the R-component image and that of the B-component image are produced.

When n=N, that is, when the surface unevenness detection at the final position in the tire radial direction is completed, the procedure goes to step S25, where an appearance inspection of the tire 20 is performed by the appearance inspecting means 16.

The appearance inspecting means 16 reads out data on detected surface unevenness from the storage unit 15M of the surface unevenness detecting means 15 and performs an inspection of the acceptability of the appearance of the tire 20 based on the number and size of the indentations and bumps (surface unevenness). In the present embodiment, the appearance is judged defective (rejected) when the density of bares 22 in the sidewall region 21 is higher than a predetermined density and non-defective (accepted) when it is lower than the predetermined density.

It should be appreciated that the density of uneven surface portions with greater surface inclination angles θ, which are the degrees of inclination of surface unevenness, may be added to the determination criteria in the inspection.

Thus, according to the present embodiment, a red slit light and a blue slit light are cast at a target surface S of the sidewall region 21 of a tire 20 from a first illuminating means 11 casting the red light and a second illuminating means 12 casting the blue light, which are disposed above the sidewall region 21 such that the illuminating directions are ±45 degrees, respectively, to the target surface S. And the illuminated surface is shot by a line camera 13 disposed in a position vertical to the target surface S. At the same time, two images, namely, an R-component image and a Blue-component image, are produced from the original image thus shot, and the luminance distribution waveforms are obtained therefrom. Then minute indentations and bumps, which are 5 mm or less in depth, formed in the target surface S are detected. Therefore, small bares 22 which have defied detection in the past can be detected also. This will improve the accuracy of appearance inspection of the tire 20.

Also, the illuminated portion of the target surface S is shot with slit lights of mutually different wavelengths cast simultaneously from mutually different directions thereat using a first illuminating means 11 and a second illuminating means 12. Thus, minute surface unevenness can be detected easily because two luminance distribution waveforms separable from each other can be obtained by a single shooting.

In such an arrangement, the surface inclination angle θ, which represents the degree of uneven surface inclination of the target surface S may be calculated using the incident direction of illuminating light from the first illuminating means 11, the incident direction of illuminating light from the second illuminating means 12, the ratio of intensity of the illuminating lights of different wavelengths, and the ratio of luminance of the reflected images of different wavelengths. Then, minute surface unevenness can be detected with certainty because the noise of stains, discolorations, and the like can be removed.

In the embodiment described thus far, there are two illuminating means, namely, a first illuminating means 11 and a second illuminating means 12, but the arrangement may be such that three or more illuminating means are provided. In such a case, too, it goes without saying that the illuminating means cast their respective slit lights of mutually different wavelengths from mutually different directions at the target surface of the object under inspection.

Also, used in the above-mentioned embodiment are the red light of the first illuminating means 11 and the blue light of the second illuminating means 12, but the arrangement is not limited thereto. The arrangement will work if the wavelengths of the illuminating lights differ from each other. However, if the difference in wavelength between the two illuminating lights is small, their separation at the image processing means 14 will be difficult and the error in luminance value after the separation large. Therefore, it is preferable that the red light and the blue light are used as in the present embodiment.

Also, in the above-described embodiment, the line camera 13, the first illuminating means 11, and the second illuminating means 12 are disposed in the same plane, and at the same time the first illuminating means 11 and the second illuminating means 12 are disposed in positions symmetrical to each other with respect to the shooting direction of the line camera 13. However, it is not always necessary that the line camera 13, the first illuminating means 11, and the second illuminating means 12 are arranged in such positions. Yet, the arrangement of the line camera 13, the first illuminating means 11, and the second illuminating means 12 as in the present embodiment can further improve the detection accuracy of surface unevenness because it allows the acquisition of reflected images of the illumination of uneven surface spots with slit lights from front and back or from right and left.

Also, in the above-described embodiment, the incident direction of illuminating light from the first illuminating means 11 is 45 degrees, and the incident direction of illuminating light from the second illuminating means 12 is −45 degrees. However, if the incident directions are within a range of 30 to 60 degrees, then the two luminance distribution waveforms can be distinguished from each other satisfactorily. It is to be noted, however, that if the incident direction is less than 30 degrees, there are possibilities that minute surface unevenness cannot be detected easily due to the shadows made by tire markings of characters and numbers formed on the sidewall region 21. On the other hand, if the incident direction is in excess of 60 degrees, detection of small surface unevenness becomes difficult because the angle of the reflected lights gets close to verticality.

Also, in the above-described embodiment, a description has been given of the detection of bares 22 occurring in the sidewall region 21 of the tire 20, but the application is not limited thereto. The embodiment can be applied to the detection of minute surface unevenness in other parts of the tire 20, such as the tire tread region. Moreover, the present invention can be applied to the appearance inspection not only of the tire 20 but also of parts and products in the manufacturing process, such as tread rubber or other rubber parts and resin moldings, which may have minute unevenness on the surface.

Also, as in the present embodiment, if the illuminated portion of the target surface S is shot with slit lights of mutually different wavelengths cast simultaneously from mutually different directions thereat using a first illuminating means 11 and a second illuminating means 12, then it is possible to obtain two luminance distribution waveforms separable from each other by a single shooting. However, use of monochromatic light or white light for the first and second illuminating means 11 and 12 and shooting the same portion two times may also allow the acquisition of two luminance distribution waveforms separable from each other. In this case, the first shooting is done with a slit light cast from the first illuminating means 11 only, and the second shooting is done with a slit light cast from the second illuminating means 12 only. Then a comparison may be made between the luminance distribution waveform derived from the image obtained by the first shooting and that derived from the image obtained by the second shooting. Also, in the above case of shooting two times, the arrangement may be such that only one illuminating means is used, and the first shooting is done with the illuminating means 11 disposed in the position of the first illuminating means 11 and the second shooting is done with the illuminating means moved to the position of the second illuminating means 12. Yet, when a monochromatic light or a white light is used, position adjustment must be carried out between the image obtained by the first shooting and one obtained by the second shooting by using a section of a character in a tire marking as the reference line, for instance. Therefore, it is preferable that slit lights of mutually different wavelengths are used as in the present embodiment.

According to the present invention, surface unevenness of a relatively shallow depth on the surface of an object under inspection can be detected, so that the accuracy of the appearance inspection of the object under inspection can be improved.

It should be understood by those skilled in the art that various modifications and variations can be made to this invention without departing from the scope and spirit of the invention. For example, the specific constituent members described herein may take all kinds of form or configuration. In addition, the relative motions of the parts between one another may be accomplished by all kinds of structures and apparatuses. Accordingly, the invention is intended to include all such modifications and variations as fall within the scope of the appended claims and the equivalents thereof.

NUMERAL REFERENCE 10 tire appearance inspection apparatus
11 first illuminating means
12 second illuminating means
13 line camera
14 image processing means
15 surface unevenness detecting means
15a luminance distribution waveform calculating unit
15b peak interval calculating unit
15c surface inclination angle calculating unit
15d determination unit
15M storage unit
16 appearance inspecting means
20 tire
21 sidewall region
22 bare
22a, 22b inside wall of bare
24 surface unevenness (indentations and bumps)
31 motor
32 rotary table
33 motor control means
34 rotation angle detecting means

The invention claimed is:

1. A method for detecting surface unevenness of an object under inspection, comprising:
shooting a reflected image of slit lights, while moving the object under inspection relative to first and second illuminators, among a plurality of illuminators, for casting the slit lights at a target surface of the object and an image pick up for shooting the illuminated portion;
detecting surface unevenness of the object under inspection based on respective luminance of the reflected image,
wherein, in the shooting, the first illuminator casts slit light at a target surface of the object under inspection and the second illuminator casts slit light having a different wavelength from the slit light of the first illuminator simultaneously from a different direction than the first illuminator at the target surface of the object under inspection, and the image pickup shoots the reflected image of the portion illuminated by the slit lights, and
wherein, in the detecting the surface unevenness, the reflected image is separated into the reflected images for mutually different wavelengths by image processing of the reflected image and luminance distribution waveforms for the separated reflected images respectively are obtained; and
surface unevenness of the object under inspection is detected based on the obtained luminance distribution waveforms of the reflected images of the mutually different wavelengths.

2. An apparatus for detecting surface unevenness of an object under inspection, comprising:
a first illuminator, among a plurality of illuminators, for casting slit light at a target surface of the object under inspection;
a second illuminator, among the plurality of illuminators, for casting slit light at the target surface of the object under inspection from a different direction than the first illuminator;
an image pickup for shooting a portion illuminated by the slit lights;
a mover for moving the first and second illuminators and the image pickup and the object under inspection relative to each other; and
a surface unevenness detector for detecting surface unevenness of the object under inspection based on luminance of a slit image shot by the image pickup,
wherein a wavelength of the slit light cast from the first illuminator differs from a wavelength of the slit light cast from the second illuminator,
wherein the image pickup shoots a reflected image of the portion where the slit lights reflect from the plurality of illuminators, and
wherein the surface unevenness detector obtains luminance distribution waveforms for the mutually different wavelengths by image processing of the reflected image to separate it into reflected images for the mutually different wavelengths and detects surface unevenness of the object under inspection based on the luminance distribution waveforms obtained for the obtained mutually different wavelengths.

3. The apparatus for detecting surface unevenness of an object under inspection as recited in claim 2, wherein the surface unevenness detector further comprises a calculator for calculating a degree of uneven surface inclination in the target surface of the object under inspection, using the incident directions of the plurality of illuminating lights to the target surface of the object under inspection, the ratio of intensity of the plurality of illuminating lights of different wavelengths, and the ratio of luminance of reflected images for the respective wavelengths, and a detector for detecting surface unevenness of the target surface by comparing the calculated degree of inclination against a preset threshold value.

4. The apparatus for detecting surface unevenness of an object under inspection as recited in claim 2, wherein the image pickup is installed between the first illuminator and the second illuminator in a same plane as the first and second illuminators so as to shoot the reflected image of the slit lights from the first and second illuminators.

5. The apparatus for detecting surface unevenness of an object under inspection as recited in claim 4, wherein the image pickup is installed in a direction vertical to the target surface of the object under inspection, and wherein the first and second illuminating units are disposed in a plane defined by the image pickup means and a direction of motion of the object under inspection and also in positions symmetrical to each other with respect to the shooting direction of the image pickup.

6. The apparatus for detecting surface unevenness of an object under inspection as recited in claim 5, wherein the illuminating directions of the first and second illuminators are within a range of 30 to 60 degrees to the target surface, respectively.

7. The apparatus for detecting surface unevenness of an object under inspection as recited in claim 4, wherein the slit light from one of the first and second illuminators is a blue light and the slit light from the other thereof is a red light.

* * * * *